United States Patent
Faust et al.

(10) Patent No.: US 12,060,561 B2
(45) Date of Patent: Aug. 13, 2024

(54) USE OF CONSTITUTIVELY ACTIVE VARIANTS OF GROWTH FACTOR RECEPTORS AS SELECTION MARKERS FOR THE GENERATION OF STABLE PRODUCER CELL LINES

(71) Applicant: CEVEC Pharmaceuticals GmbH, Cologne (DE)

(72) Inventors: Nicole Faust, Cologne (DE); Silke Wissing, Cologne (DE); Nikola Strempel, Cologne (DE)

(73) Assignee: CEVEC Pharmaceuticals GmbH, Cologne (DE)

( * ) Notice: Subject to any disclaimer, the term of this patent is extended or adjusted under 35 U.S.C. 154(b) by 824 days.

(21) Appl. No.: 16/636,622

(22) PCT Filed: Aug. 1, 2018

(86) PCT No.: PCT/EP2018/070829
§ 371 (c)(1),
(2) Date: Feb. 4, 2020

(87) PCT Pub. No.: WO2019/030069
PCT Pub. Date: Feb. 14, 2019

(65) Prior Publication Data
US 2020/0377895 A1    Dec. 3, 2020

(30) Foreign Application Priority Data
Aug. 8, 2017 (EP) .................................. 17001356

(51) Int. Cl.
| C07K 14/705 | (2006.01) |
| C07K 14/71 | (2006.01) |
| C07K 19/00 | (2006.01) |
| C12N 5/07 | (2010.01) |
| C12N 5/071 | (2010.01) |
| C12N 5/10 | (2006.01) |
| C12N 5/16 | (2006.01) |
| C12N 15/09 | (2006.01) |
| C12N 15/113 | (2010.01) |
| C12N 15/62 | (2006.01) |
| C12N 15/63 | (2006.01) |
| C12N 15/85 | (2006.01) |

(52) U.S. Cl.
CPC ........ *C12N 15/62* (2013.01); *C07K 14/70517* (2013.01); *C07K 14/71* (2013.01); *C07K 19/00* (2013.01); *C12N 5/06* (2013.01); *C12N 5/0625* (2013.01); *C12N 5/10* (2013.01); *C12N 5/16* (2013.01); *C12N 15/09* (2013.01); *C12N 15/1138* (2013.01); *C12N 15/63* (2013.01); *C12N 15/85* (2013.01); *C07K 2319/00* (2013.01); *C12N 2501/105* (2013.01)

(58) Field of Classification Search
CPC .......... C12N 5/0006; C12N 5/00; C12N 5/10; C12N 15/01; C12N 15/09; C12N 15/63; C07K 14/705; C07K 14/70517; C07K 14/71; C07K 14/70596; C07K 19/00; C07K 2319/00
See application file for complete search history.

(56) References Cited

U.S. PATENT DOCUMENTS

| 5,262,308 | A | | 11/1993 | Baserga | |
| 5,958,685 | A | * | 9/1999 | Ebina | ..................... C07K 14/72 |
| | | | | | 536/24.31 |
| 7,265,260 | B2 | | 9/2007 | Bol et al. | |
| 8,357,661 | B2 | | 1/2013 | Brinkman et al. | |
| 10,995,128 | B2 | | 5/2021 | Cottingham et al. | |
| 2003/0182668 | A1 | | 9/2003 | Bol et al. | |
| 2004/0014024 | A1 | * | 1/2004 | Yayon | ................ G01N 33/5011 |
| | | | | | 435/7.2 |
| 2009/0214513 | A1 | * | 8/2009 | Zhong | ....................... A61P 5/18 |
| | | | | | 435/69.51 |
| 2010/0028951 | A1 | | 2/2010 | Hamilton | |
| 2012/0301447 | A1 | * | 11/2012 | Jensen | ................... A61K 35/17 |
| | | | | | 435/372.3 |
| 2012/0322738 | A1 | | 12/2012 | Behrens | |
| 2013/0040897 | A1 | | 2/2013 | Markus | |

(Continued)

FOREIGN PATENT DOCUMENTS

| CN | 101 613 678 A | 12/2009 |
| JP | 2013519636 | 5/2013 |

(Continued)

OTHER PUBLICATIONS

Kim et al. Constitutively active type I insulin-like growth factor receptor causes transformation and xenogradt growth of immortalized mammary epithelial cells and is accompanied by an epithelial-to-mesenchymal transition mediated by NF-KB and Snail. Mol Cell Biol 27(8): 3165-3175, 2007.*

(Continued)

*Primary Examiner* — Bridget E Bunner
(74) *Attorney, Agent, or Firm* — Eversheds Sutherland (US) LLP (57) ABSTRACT

The present invention relates to methods for the selection of a stable producer cell line expressing one or more protein(s) of interest (POIs), comprising the stable transfection of cells with a gene encoding a constitutively active variant of a growth factor receptor, respective methods for the expression of one or more POIs in such stable producer cell lines, and uses of a constitutively active variant of a growth factor receptor as selection marker in the cultivation of cells.

11 Claims, 3 Drawing Sheets
Specification includes a Sequence Listing.

(56) References Cited

U.S. PATENT DOCUMENTS

2016/0152723 A1* 6/2016 Chen .............. A61K 35/17
                                                435/254.2
2017/0020992 A1   1/2017 Bolt

FOREIGN PATENT DOCUMENTS

| RU | 2479629 | 3/2008 |
|---|---|---|
| WO | WO-2006113861 A2 * | 10/2006 |
| WO | WO 2008/077547 | 7/2008 |
| WO | WO 2010/12793 | 11/2010 |
| WO | WO-2011056894 A2 * | 5/2011 |
| WO | WO 2013/093760 | 6/2011 |
| WO | WO2011/101267 | 8/2011 |
| WO | WO 2012/077128 | 6/2012 |
| WO | WO2012/093760 | 7/2012 |
| WO | WO 2014/015227 | 1/2014 |
| WO | WO 2014/140927 | 9/2014 |

OTHER PUBLICATIONS

Litzenburger et al. BMS-536924 reverses IGF-IR-induced transformation of mammary epithelial cell and causes growth inhibition and polarization of MCF7 cells. Clin Cancer Res 15(1): 226-237, 2009.*

Carboni et al. Tumor Development by Transgenic Expression of a Constitutively Active Insulin-Like Growth Factor I Receptor. Cancer Res 65(9): 3781-3787, 2005.*

Wissing, S. et al, Expression of glycoproteins with excellent glycosylation profile and serum half-life in CAP-Go cells, 2015, BMC Proceed. vol. 9, p. 12.

Backstrom et al., Recombinant MUC1 mucin with a breast cancer like O-glycosylation produced in large amounts in CHO cell, 2003, Biochem. J. vol. 376, pp. 677-686.

Blanchard et al., N-glycosylation and biological activity of recombinant human alpha-antitrypsin expressed . . . , 2011, Biotechnol Bioengin vol. 108, pp. 2118-2128.

Blixt et al, Efficient chemoenzymatic synthesis of O-linked sialyl oligosaccharides, 2002, J. Am. Chem. Soc. vol. 124, pp. 5739-5746.

Castilho et al., N-glycosylation engineering of plants for the biosynthesis of glycoproteins with bisected and branched . . . , 2011, Gycobiology vol. 21, pp. 813-823.

Cheung et al., Metabolic homeostasis and tissue renewal are dependent on 1,6GlcNAc-branched N-glycans, 2007, Glycobiology vol. 17, pp. 828-837.

Schiedner et al, Efficient and reproducible generation of high-expressing, stable human cell lines without need for antibiotic . . . , 2008, BMC Biotechnol. vol. 8, :13.

Dalziel et al., The relative activities of the C2GnT1 and ST3Gal-I glycosyltransferases determine the O-Glycan tumor . . . , 2000, J. Biol. Chem. vol. 276, pp. 11007-11015.

Fukuta et al., Genetic engineering of CHO cells producing human interferon-g by transfection of sialyltransferases, 2000, Glycoconjug. J. vol. 17, pp. 895-904.

Guo et al., Effect of N-acetylglucosaminyltransferase V on the expression of other glycosyltransferases, 2004, FEBS Lett vol. 562, pp. 93-98.

Kojima et al., Kinetic properties and acceptor substrate preferences of two kinds of GalP1, 3GalNAc cu-2,3-sialyltransferase . . . , 1994, Biochemistry vol. 33, pp. 5772-5776.

Kono et al, Mouse beta-galactoside alpha-2,3-sialyltransferases: comparison of in vitro substrate . . . , 1997, Glycobiology, Oxford University Press, vol. 7, pp. 469-479.

Lee et al., N-glycan analysis of human alpha1-antitrypsin produced in Chinese hamster ovary cells, 2013, Gycoconjug J vol. 30, pp. 527-547.

Lusch et al., Development and analysis of alpha1-antitrypsin neoglycoproteins: the impact of additional N-glycosylation . . . , 2013, Molc Pharmaceut vol. 10, pp. 2616-2629.

Niimi et al., High expression of N-acetylglucosaminyltransferase IVa promotes invasion of choriocarcinoma, 2012, Brit J Cancer vol. 107, pp. 1969-1977.

Priatel et al, The ST3Gal-1 Sialyltransferase controls CD8+ T-Lymphocyte homeostasis by modulating O-glycan biosynthesis, 2000, Immunity vol. 12, pp. 273-283.

Shang et al, Molecular cloning and expression of Galb1,3GalNAc a2,3-sialyltransferase from human fetal liver, 1999, Eur. J. Biochem. vol. 265, pp. 580-588.

Thim et al., Purification and characterization of a new recombinant factor VIII (N8), 2010, Haemophilia vol. 16, pp. 349-359.

Vallejo-Ruiz et al, Delineation of the minimal catalytic domain of human Galbetal-3GalNAc-alpha-2,3-sialyltransferase, 2001, Biochim Biophys Acta vol. 1549, pp. 161-173.

Wang et al., Structural characterization of recombinant alpha1-antitrypsin expressed in a human cell line, Analy Biochem vol. 437, pp. 20-28 2013.

Whitehouse et al., A transfected sialyltransferase that is elevated in bresat cancer and localizes to the medial/trans-Golgi . . . , 1997, J. Cell Biol, vol. 137, pp. 1229-1241.

Yin et al., Glycoengineering of Chinese hamster ovary cells for enhanced erythropoietin N-glycan branching and sialylation, Biotechnol Bioengin vol. 112, pp. 2343-2351 2015.

Zhang et al, Relations of the type and branch of surface N-glycans to cell adnesion, migration and integrin expression, 2004, Molc Cell Biochem vol. 260, pp. 137-146.

Chejanovsky et al, Mutagenesis of an AUG codon in the adeno-associated virus rep gene, effects on viral DNA replication, 1989, Virol. vol. 173, pp. 120-128.

* cited by examiner

USE OF CONSTITUTIVELY ACTIVE VARIANTS OF GROWTH FACTOR RECEPTORS AS SELECTION MARKERS FOR THE GENERATION OF STABLE PRODUCER CELL LINES

This application is a is a 371 of PCT/EP2018/070829, having an international filing date of Aug. 1, 2018, which claims the benefit of European Patent Application Serial No. 17001356.9, filed Aug. 8, 2017, the content of which is incorporated by reference in its entirety.

The official copy of the Sequence Listing is submitted concurrently with the specification as an ASCII formatted text file via EFS-Web, with a file name of "CVC006_ST25 txt", a creation date of Jan. 9, 2020, and a size of 8000 bytes. The Sequence Listing filed via EFS-Web is part of the specification and is incorporated in its entirety by reference herein.

The present invention relates to methods for the selection of a stable producer cell line expressing one or more protein(s) of interest (POIs), comprising the stable transfection of cells with a gene encoding a constitutively active variant of a growth factor receptor, respective methods for the expression of one or more POIs in such stable producer cell lines, and uses of a constitutively active variant of a growth factor receptor as selection marker in the cultivation of cells.

Selection markers are essential tools for the generation of stable producer cell lines, i.e., cell lines that stably express one or more POIs such as e.g. biopharmaceuticals. Usually, these selection markers are antibiotic resistance genes which are encoded on the expression vector, and which are stably integrated in the target genome (e.g. by transfection) together with the gene(s) of interest (GOIs). Cultivation of the transfected cells in the presence of the respective antibiotic selects for producer cells with integrated expression vector.

Commonly used antibiotic-based selection markers for mammalian expression systems include e.g. Blasticidin S resistance genes from *Bacillus cereus* or *Aspergillus terreus*, G418 (Geneticin) resistance gene from transposon Tn5 (neo), Puromycin resistance gene from *Streptomyces* spp., Hygromycin B resistance gene from *Escherichia coli*, and Zeocin resistance gene from *Streptoalloteichus hindustanus*.

Drawbacks of antibiotic resistance-based selection markers include the fact that only a very limited set of selection markers is available. Further, there are issues with instable producer clones, especially when expressing very large, multimeric proteins, wherein recombinant expression of the target protein is silenced over time resulting in low titers during production. To prevent silencing, the cells can be cultured in the presence of the respective antibiotic selection agent. However, the large scale production of POIs in the presence of antibiotics is not desirable as this requires extensive removal and analytics steps after production.

Thus, there is an urgent need for new selection markers, e.g. in case that several expression constructs need to be stably integrated, allowing for enhanced stability of cell lines and ease of use. Ideally, such new selection markers support the sustained expression of the POI in the absence of selection agents.

Accordingly, the technical problem underlying the present invention is to provide respective selection markers and methods using the same.

The solution to the above technical problem is achieved by the embodiments characterized in the claims.

In particular, in a first aspect, the present invention relates to a method for the selection of a stable producer cell line expressing one or more protein(s) of interest (POIs), comprising the steps of:
(a) providing a cell line,
(b) concurrently stably transfecting said cell line with
    (i) a gene encoding a constitutively active variant of a growth factor receptor, wherein growth of said cell line in the absence of expression of said constitutively active variant of a growth factor receptor is dependent on the growth factor that is recognized by said growth factor receptor, and
    (ii) one or more gene(s) of interest (GOIs) encoding said POIs, and
(c) cultivating said cell line in a cell culture medium either not containing the growth factor that is recognized by said growth factor receptor or containing said growth factor at concentrations which are too low to support growth of the cells in the absence of expression of said constitutively active variant of a growth factor receptor.

Usually, growth factor receptors are activated by binding of the respective ligand, i.e., the respective growth factor (e.g. IGF-1, IFG-2 or insulin for IGF-1R), and subsequent dimerization leading to downstream phosphorylation events and activation of growth-promoting and anti-apoptotic pathways, including MAP-Kinase and NFkappaB pathways. These growth factors are present in serum and need to be supplemented when cultivating cells which are dependent on these factors in serum-free growth medium. Cells which show a growth response to IGF-1 and insulin include CAP, CHO, BHK, HEK 293, Vero, PER.C6®, MDCK cells, hybridoma cells, and fibroblasts. Cultivation of such cells usually requires supplementation of growth factors which increases the costs of respective production processes. The present invention realizes a new approach, i.e., the stable integration of constitutively active growth factor receptor variants and positive selection by growth factor depletion in the cell culture medium, allowing for production in protein-free medium.

The term "selection" as used herein refers to a process of allowing the exclusive survival and proliferation of desired positive cell clones by establishing a selection pressure, i.e., according to the present invention, cultivating said cells in a cell culture medium either not containing the growth factor that is recognized by said growth factor receptor or containing said growth factor at concentrations which are too low to support growth of the cells in the absence of expression of said constitutively active variant of a growth factor receptor, whereas not desired negative cell clones are not able to survive and proliferate under said selection pressure. This use of the term "selection" is to be clearly distinguished from the physical isolation and/or enrichment of desired cells, e.g. by sorting or attachment, out of a larger pool of cells.

The term "producer cell line" as used herein relates to cell lines producing, i.e., expressing, one or more POIs. The term "stable producer cell line" in this respect refers to the fact that the gene(s) encoding said POIs (gene(s) of interest; GOIs), as well as the gene encoding the constitutively active variant of a growth factor receptor, are stably integrated into the cell genome.

In specific embodiments, the cell line provided in step (a) of the methods of the present invention is a mammalian cell line, including a human cell line. Preferably, the cell line is selected from the group consisting of CHO cells, HEK293 cells, CAP cells, Per.C6 cells, BHK cells, Vero cells, MDCK cells, hybridoma cells, and fibroblasts. More preferably, the cell is a CAP cell line.

POIs to be expressed by the cell lines used in the present invention are not particularly limited. They include any proteins expression of which might be desired, for example proteins that are selected from the group consisting of extracellular matrix proteins, growth factors, peptide hormones, cytokines, enzymes, antibodies, antibody fragments, blood clotting factors, protease inhibitors, and viral protein products. Specific examples include human recombinant alpha-1-antitrypsin (rhAAT), fibrinogen, laminins (LAM), interferons (IFN), interleukins (IL), Immunglobulin G (IgG), Immunglobulin M (IgM), bispecific monoclonal antibodies (BsAb), erythropoietin (EPO), Factor VII (FVII), Factor VIII (FVIII), Factor IX (FIX), von-Willebrand-Factor (vWF), C1 esterase inhibitor (C1-inhibitor; C1 Inh), gag-pol from HIV-1, HIV-2, EIAV, SIV, or other retroviridae (gag-pol), rep protein from Adeno-Associated Virus (REP), cap protein from Adeno-Associated Virus (CAP) and variants thereof.

In step (b) of the methods of the present invention, the cell line is stably transfected with (i) a gene encoding a constitutively active variant of a growth factor receptor, wherein growth of said cell line in the absence of expression of said constitutively active variant of a growth factor receptor is dependent on the growth factor that is recognized by said growth factor receptor, and (ii) one or more GOIs encoding said POIs. Respective transfection methods are not particularly limited and are known in the art.

The term "stably transfecting" as used herein indicates the fact that the respective genes are stably integrated into the cell genome.

The term "wherein growth of said cell line in the absence of expression of said constitutively active variant of a growth factor receptor is dependent on the growth factor that is recognized by said growth factor receptor" indicates the fact that in order for the method of the present invention to work as desired, the growth factor receptor 1 growth factor has to be selected such that growth of the cells under native conditions, i.e., in the untransfected cells, is dependent on said growth factor and respective growth factor receptor signaling.

The term "constitutively active variant of a growth factor receptor" relates to growth factor receptor variants that are in an activated state even in the absence of their respective growth factor ligand.

In a preferred embodiment, the gene encoding a constitutively active variant of a growth factor receptor and the GOIs are present on the same vector. Suitable vectors are not particularly limited and are known in the art.

In specific embodiments, the growth factor receptor and respective growth factors are IGF-1R (insulin-like growth factor 1 receptor), IR (insulin receptor), and IGF-1, IGF-2 and/or insulin; EGFR (epidermal growth factor receptor) and respective EGFR ligands; FGFR (fibroblast growth factor receptor) and FGFs; or PDGFR (platelet-derived growth factor receptor) and PDGFs.

In specific embodiments, the constitutively active variant of a growth factor receptor is an extracellular domain-deleted EGFR, a ZNF198-FGFR1 fusion protein, a PDGFR with point mutations, an IR with point mutations, a constitutively active variant of an extracellular domain-deleted IGF-1R (IGF1R TM-icd) and point mutations thereof to increase activation, as known in the art.

In a particular embodiment, the constitutively active variant of a growth factor receptor is a human CD8-IGF-1R fusion protein. Preferably, said fusion protein comprises or consists of the amino acid sequence of SEQ ID NO: 1. Further, said human CD8-IGF-1R fusion protein is preferably encoded by a nucleic acid comprising or consisting of the nucleotide sequence of SEQ ID NO: 2.

In step (c) of the methods of the present invention, the cell line is cultivated in a cell culture medium either not containing the growth factor that is recognized by said growth factor receptor or containing said growth factor at concentrations which are too low to support growth of the cells in the absence of expression of said constitutively active variant of a growth factor receptor. In this context, respective concentrations which are too low in this respect depend on the specific growth factor and growth factor receptor and can be easily determined by the person skilled in the art. This step is preferably performed for a duration that allows selection to occur, i.e., for a duration that is long enough to allow for the death of cells not expressing the constitutively active variant of the growth factor receptor. In specific examples, step (c) is performed for 9 or 10 passages. In this context, the duration that allows selection to occur is dependent on several factors, including but not limited to the composition of the cell culture medium, the cell line and regulatory elements which are present on the expression vector and may therefore vary depending on these factors. Respective durations can be easily determined by the person skilled in the art.

In a second aspect, the present invention relates to a method for the expression of one or more protein(s) of interest (POIs) in a stable producer cell line, comprising the steps of:
  (a) performing the method according to the first aspect of the present invention, as defined above,
  (b) expressing said POIs in said stable producer cell line, and
  (c) recovering said POIs from the cells or the cell culture medium.

Methods for the expression of POIs in a cell line and the recovery thereof are not particularly limited and are known in the art.

Further, all definitions and limitations defined for the first aspect of the present invention apply to this second aspect of the present invention in an analogous manner.

In a third aspect, the present invention relates to the use of a constitutively active variant of a growth factor receptor as selection marker in the cultivation of cells.

In this aspect, all definitions and limitations defined for the first aspect of the present invention apply to this third aspect of the present invention in an analogous manner. In particular, the cells, growth factor receptors, growth factors, and constitutively active variants of growth factor receptors are as defined above.

The present invention is based on the idea of using constitutively active growth factor receptors (e.g. of IGF-1R) as selection markers. This advantageously adds new, efficient selection markers to the limited panel of currently available selection markers, in particular for mammalian expression systems. Further, the present invention allows for continuous selection pressure during cultivation of producer cells, providing the potential of stabilizing the expression of difficult-to-express target proteins without need of later removal of the selection agent and time-consuming, expensive analytics to prove the absence of the selection agent in the final product. Moreover, the present invention advantageously allows for a cost reduction in large-scale production processes, as there is no need for supplementation of serum-free cell culture medium with the respective growth factors.

The above possibility of establishing a continuous selection pressure, without having to provide additional reagents, is a significant advantage of the methods and uses of the present invention. It allows for the maintenance of high yield expression of recombinant proteins, in particular in cases where a producer cell line is not stably expressing said proteins over several passages. In this context, it should be noted that such unstable producer cell lines are quite common, in particular when protein expression is very high, since excessive protein expression can negatively impact proliferation rates and the cells have a survival and proliferation advantage when shutting down protein production. This silencing effect is advantageously and efficiently countered by establishing a continuous selection pressure according to the present invention.

The figures show:

FIG. 1A and FIG. 1B:

CAP cell pools stably expressing recombinant human alpha-1-antitrypsin (rhAAT) were generated by transfection of parental CAP cells with either pStbI-CD8-IGF1R-AAT or pStbI-bsd-AAT (control) following selection in IGF-1 depleted or blasticidin containing CAP-CDM growth medium. Mock transfected CAP cells were cultivated in CAP-CDM containing 50 µg/L Long-R3-IGF or in CAP-CDM without IGF over 10 passages as a control. For all pools, cells were grown in 125 mL shake flasks at 185 rpm, 5% $CO_2$ and 37° C. and were passaged every 72-96 h while adjusting the viable cell density (VCD) to $1\times10^6$ cells/mL.

FIG. 2:

RhAAT levels in cell culture supernatants from fed-batch cultures of CAP-bsd-AAT and CAP-CD8-IGF1R-AAT pool cells taken on day 10. RhAAT titers were quantified by ELISA.

The present invention will be further illustrated in the following examples without being limited thereto.

EXAMPLES

Example 1

Generation of CAP cells stably expressing human recombinant alpha-1-antitrypsin (AAT) by use of a constitutively active CD8-IGF1R variant as a selection marker.

INTRODUCTION

CAP cells are human amniocyte-derived suspension cells which show a growth inhibition in serum-free medium without IGF-1 or insulin supplementation. Thus, they are a suitable cell line for implementation of the new selection marker according to the present invention.

IGF-1R is a transmembrane receptor tyrosine kinase which is essential for cell growth and protein biosynthesis by activating PI3K/Akt-kinase+mTOR and MAP kinase pathways. It is a tetramer comprising two alpha-subunits and two beta-subunits. Its ligands are IGF-1 (highest affinity), IGF-2, and insulin (lowest affinity). Binding of ligands to the alpha-subunit leads to conformational changes (dimerization of alpha-subunits) and subsequent autophosphorylation of specific tyrosine residues of the beta-subunits (Tyr1131, Tyr1135, Tyr1136, Tyr950) followed by binding of receptor substrates (IRS1-4, shc) to their binding sites and initiation of downstream signaling pathways.

Constitutive activation of IGF-1R can be achieved by fusing the intracellular and transmembrane domains thereof to the extracellular domain of human T-cell marker CD8. This method has been previously described in the art, where the CD8-IGF1R fusion construct was utilized as a tool for investigating the role of IGF1R signaling for tumor development in a mouse model. In none of the art, the recombinant expression of CD8-IGF1R and associated constitutive activation of IGF1R served as a selection marker for the generation of stable cell lines.

Alpha-1-antitrypsin (AAT) is a 52 kDa glycoprotein and serine protease inhibitor, targeting in particular neutrophil elastase. Hereditary AAT deficiency leads to severe lung emphysema. Recombinant human AAT (rhAAT) has been successfully produced in CAP cells and is used herein as a model protein for studies involving the CD8-IGF1R as a new selection marker.

Experimental Procedures:

Cloning of Expression Constructs:

Components of the CD8-IGF1R fusion protein are (i) amino acids 1-218 of the human CD8 alpha chain (Uniprot P01732-1), and (ii) amino acids 964-1367 of the intracellular domain of human IGF-1R (NCBI Protein Database NP000866). These are fused in frame without a linker, resulting in the amino acid sequence of CD8-IGF1R fusion protein (SEQ ID NO: 1, as shown hereinafter). The respective cDNA sequence is SEQ ID NO: 2, as shown hereinafter.

cDNA was synthesized by GeneArt (Thermo Fisher Scientific) and subcloned into a pStbl expression vector (CEVEC Pharmaceuticals, Germany) by replacement of the bsd resistance gene by the CD8-IGF1R construct. Components of the final expression construct pStbI-CD8-IGF1R-AAT are (i) cDNA of human alpha1-antitrypsin (AAT) under the control of CMV promoter, (ii) selection cassette containing CD8-IGF1R under the control of human Ubc promoter, (iii) enhancing element for stable transcription of integrated ORFs, (iv) pUC ori for propagation in *E. coli*, and (v) ampicillin resistance cassette for selection in *E. coli*.

Verification of the plasmid was by sequencing performed by Eurofins MWG Operon. As control vectors were used (i) pStbI-bsd-AAT (AAT cDNA under control of CMV promoter, bsd selection cassette), and (ii) pStbI-bsd (empty; no GOI, bsd selection cassette).

Cell Culture:

Parental CAP, CAP-bsd-AAT and CAP mock cells were routinely cultivated in chemically defined, serum-free CAP-CDM medium (Merck Millipore, Germany) supplemented with 6 mM L-alanyl-L-glutamine (Biochrom, Germany) and 50 µg/L Long-R3-IGF-I (SAFC, Germany) in shake flasks (125 mL; Corning) on a shaking incubator at 185 rpm (5 cm orbit), 5% $CO_2$ and 37° C.

CAP-CD8-IGF1R-AAT cells were cultivated in chemically defined, serum-free CAP-CDM medium (Merck Millipore, Germany) supplemented with 6 mM L-alanyl-L-glutamine (Biochrom, Germany) without Long-R3-IGF-I.

During routine cultivation, cells were diluted with fresh medium to a viable cell density of $1\times10^6$ cells/ml every 72-96 h. Viable cell density and viability were determined by trypan blue exclusion using a CEDEX XS cell counter (Innovatis, Roche Applied Science).

During fermentation, cells were fed on days 3, 5, and 7 with 10% (v/v) CAP-CDM feed (Merck Millipore, Germany) and 4 mM L-Alanyl-L-glutamine (Biochrom, Germany).

Nucleofection and Generation of Stable Pools:

Stable pools were generated using Lonza's Nucleofector according to the manufacturer's instructions. For each nucleofection reaction, $1\times10^7$ cells were harvested by centrifugation (150×g, 5 min). The cells were resuspended in 100 µl complete nucleofector solution V (Lonza) and mixed with 5 µg of the linearized expression vector. The DNA/cell suspension was transferred into a cuvette and the nucleofection was performed using the X001 program. The transfected cells were transferred into 12.5 mL growth medium and cultured as described before at 37° C., 5% CO₂ at 185 rpm.

For generation of stable pools, cells were pelleted by centrifugation and resuspended in selection medium (see Table 1) 72-96 h post-transfection followed by cultivation in a shaking incubator as described before.

CAP mock cells cultivated in IGF-1-depleted CAP-CDM medium served as a negative control.

TABLE 1

Generated CAP cell pools and corresponding expression vectors and media

| Cell line | Plasmid | Selection medium |
|---|---|---|
| CAP-bsd-AAT | pStbl-bsd-AAT | CAP-CDM + 6 mM L-alanyl-L-glutamine + 50 µg/L Long-R3-IGF-1 + 5 µg/mL blasticidin |
| CAP-CD8-IGF1R-AAT | pStbl-CD8-IGF1R-AAT | CAP-CDM + 6 mM L-alanyl-L-glutamine |
| CAP mock | pStbl-bsd (empty) | a) CAP-CDM + 6 mM L-alanyl-L-glutamine + 50 µg/L Long-R3-IGF-1<br>b) CAP-CDM + 6 mM L-alanyl-L-glutamine |

ELISA:

Concentrations of recombinant AAT in CAP cell culture supernatants were determined using a two-site ELISA. In this microplate-based assay, AAT is captured by an immobilized goat AAT-specific antibody and detected by a second goat AAT-specific antibody which is coupled to horseradish-peroxidase (Bethyl, Cat. #A80-122A/B).

For coating, 96-well microtiter plates were incubated with diluted capture antibody (Bethyl, 1.33 µg/mL in 0.1 M Na₂CO₃/0.1 M NaHCO₃; 100 µL/well) for 1 h at 37° C.

The wells were washed four times with TBS+0.05% (v/v) Tween-20 (=TBST; 200 µl/well) and blocked with TBST+ 5% (w/v) skim milk powder (=TBSTM; 200 µL/well) overnight at 4° C. After blocking, the plate was washed twice with TBST (200 µL/well), and AAT standard (0.2-200 ng/ml, two-fold serial dilutions in TBST), samples and negative controls were added (100 µL/well). Plates were sealed and incubated for 90 min at 37° ° C.

Next, the plate was washed four times as described above followed by addition of the detection antibody (66.7 ng/ml in TBSTM; 100 µL/well) and an 1 h incubation step at 37° C. Wells were washed as described above and the TMBD substrate (0.1 mg/ml in 24 mM citrate/52 mM Na₂HPO₄/ 0.006% H₂O₂, pH 5.0) was added (100 µL/well).

After 10 min incubation at ambient temperature the reaction was stopped by addition of 0.5 M H₂SO₄ (100 µL/well) and absorbance at 450 nm (=A450) was measured using a BioRad microtiter plate reader. A standard curve (4-parameter fit) was generated from A450 values of AAT standard dilutions. The curve was used for quantification of recombinant AAT in cell culture supernatants.

Figure 1A:
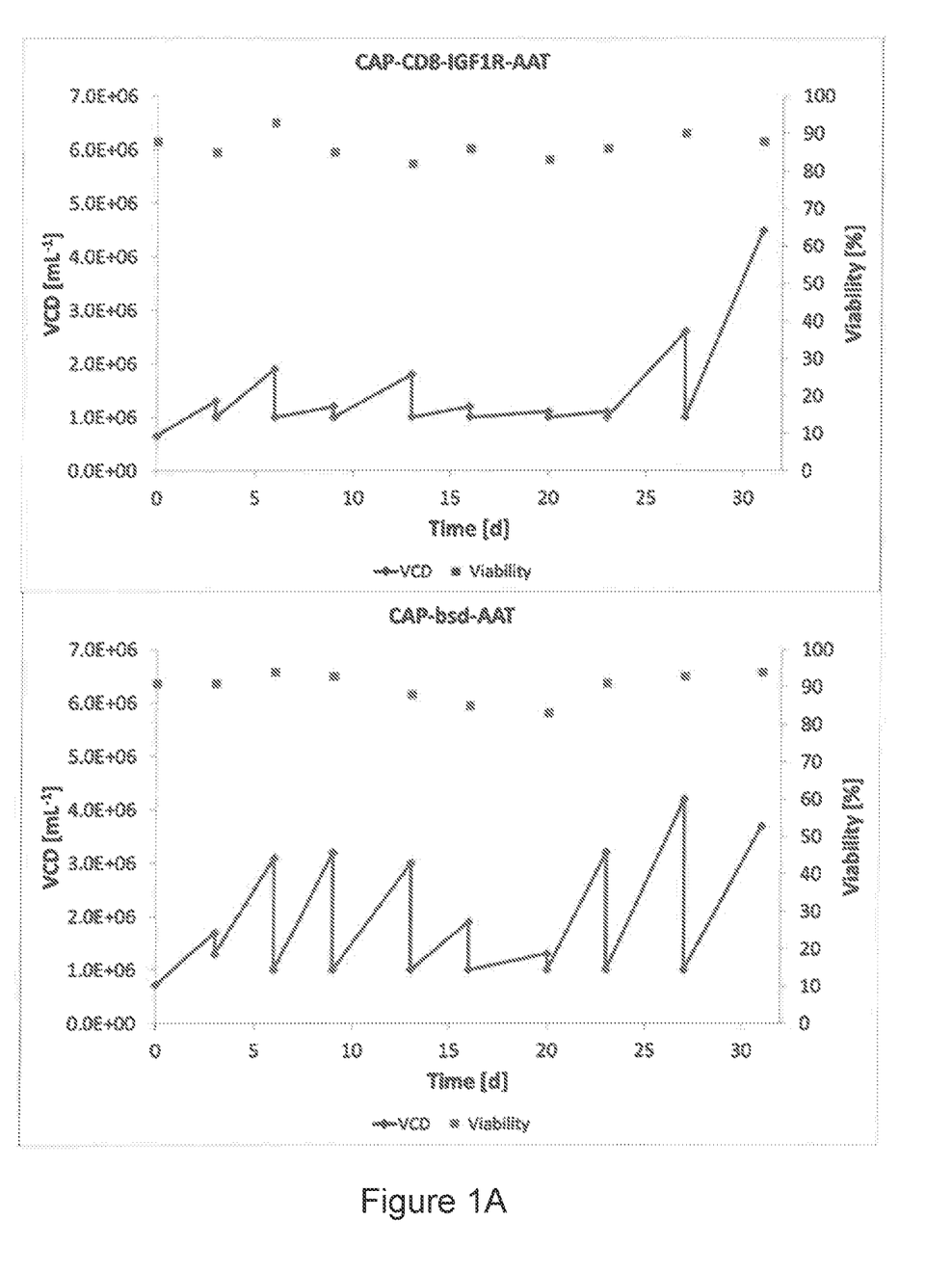
Figure 1B:
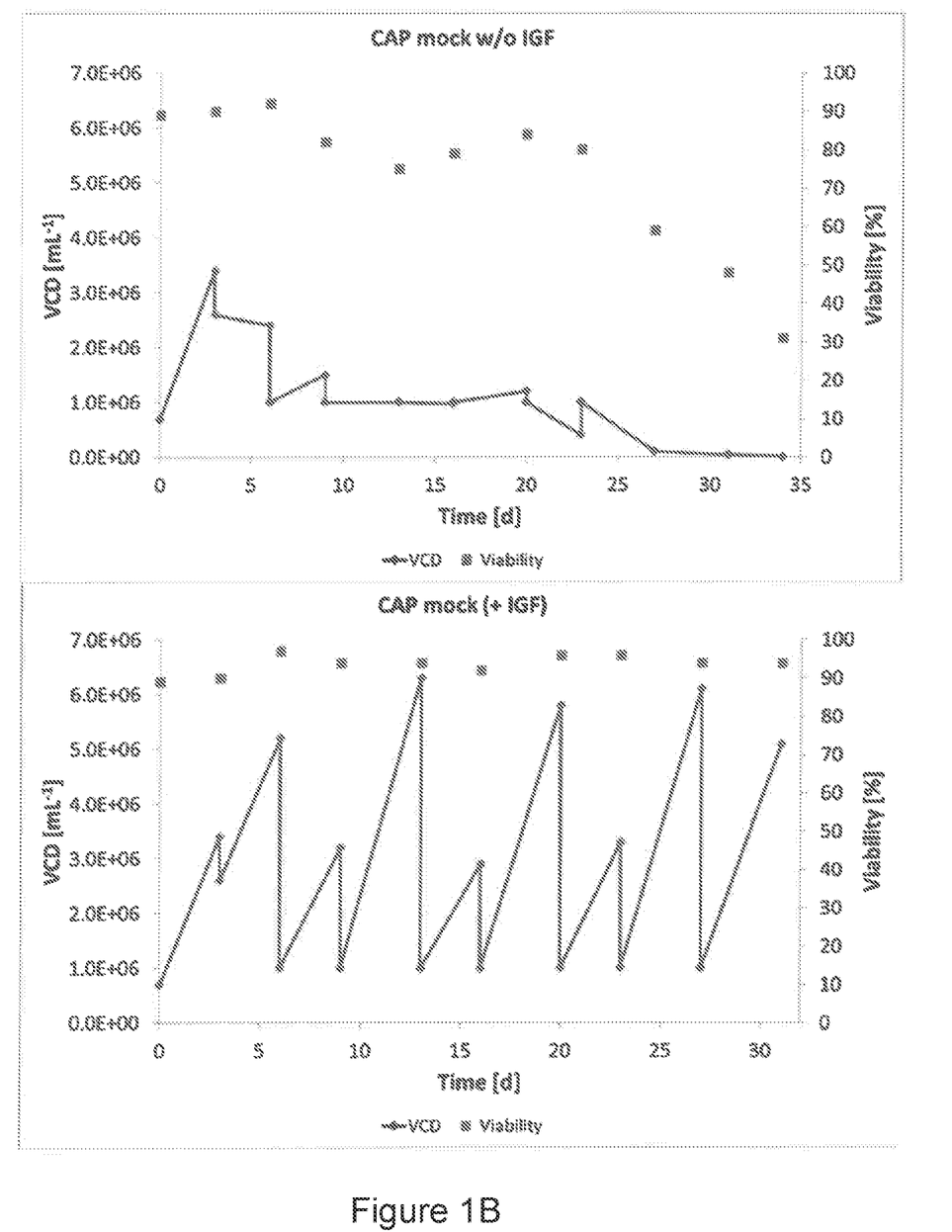

Results:

In order to prove the suitability of the constitutively active IGF1R receptor as a selection marker for the generation of stable (CAP) producer cell lines, parental CAP cells were transfected with either the CD8-IGF1R-AAT expression vector or an AAT expression vector containing a blasticidin resistance cassette as a selection marker. CAP cells transfected with the empty pStbI-bsd plasmid (CAP mock) served as a control. One passage after nucleofection, the cells were transferred into the respective selection medium (Table 1) and cultivated over a period of 9 to 10 passages. After 8 to 9 passages in IGF1-depleted growth medium, the CAP-CD8-IGF1R-AAT pool had recovered from selection and reached viable cell densities and viabilities that were comparable to the CAP mock pool which was cultivated in full growth medium containing IGF1 (>2×10⁶cells/mL, >85% viability after 72-96 h). In contrast, mock transfected CAP cells did not survive cultivation in the IGF-1 depleted growth medium, with viable cell density and viability starting to drop to <2×10⁶ cells/mL and <85% viability after 72-96 h after 3 passages already (FIGS. 1A and 1B). This data indicates that the recombinant expression of CD8-IGF1R in CAP cells indeed leads to constitutive activation of the CD8-IGF1R and related downstream signaling pathways and that this constitutive IGF1R activation can compensate IGF1 starvation and thereby allow for growth of CAP cells in IGF1-depleted cell culture medium.

Figure 2:
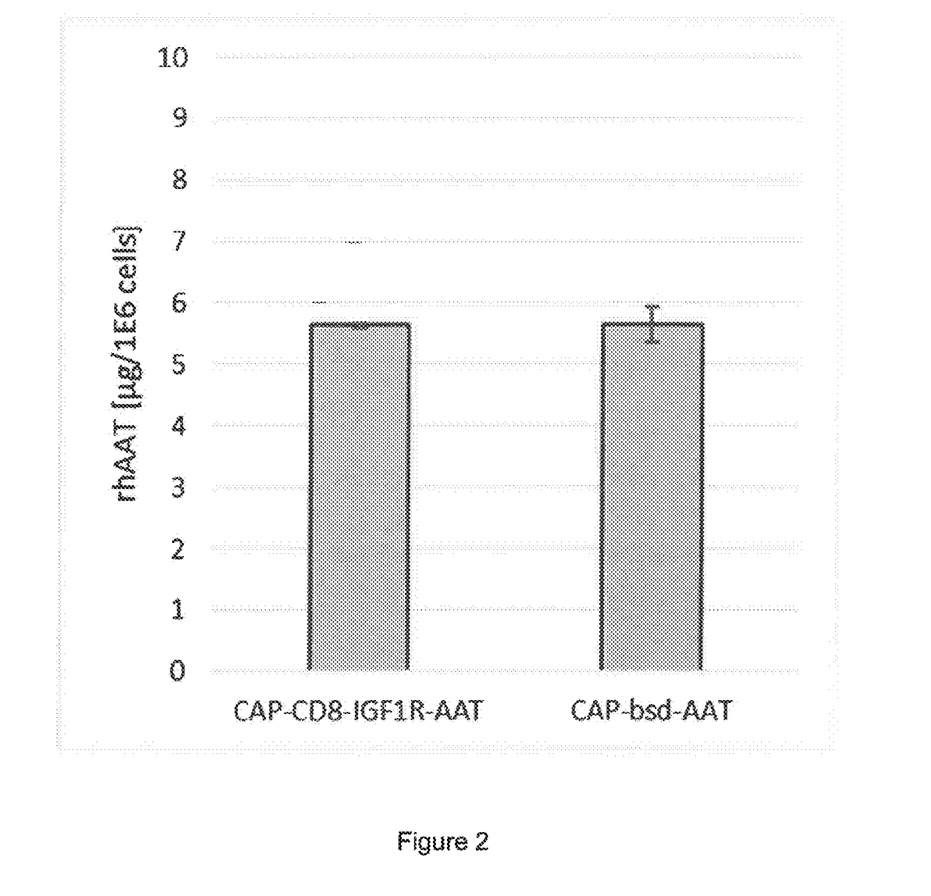

In order to compare the productivity of a CAP cell pool which was generated by conventional blasticidin selection and a CAP cell pool which was generated using the novel CD8-IGF1R selection marker, a fed-batch production run over 10 days was carried out with the stable CAP cell pools and concentrations of rhAAT in the cell culture supernatants from day 10 were quantified by ELISA. Titers were comparable for both CAP cell pools (5.6 µg AAT/1×10⁶ cells each; FIG. 2), which indicates that the generation of a stable AAT-expressing CAP cell pool by selection using the CD8-IGF1R fusion construct and IGF-1-depleted growth medium within 4 weeks was successful and that the CD8-IGF1R construct is a suitable selection marker for the generation of stable CAP cells when co-transfected with the GOI. The present invention relates to the following nucleotide sequences.

Human CD8-IGF1R fusion protein

SEQ ID NO: 1

MALPVTALLLPLALLLHAARPSQFRVSPLDRTWNLGETVELKCQVLLSNP

TSGCSWLFQPRGAAASPTFLLYLSQNKPKAAEGLDTQRFSGKRLGDTFVL

TLSDFRRENEGYYFCSALSNSIMYFSHFVPVFLPAKPTTTPAPRPPTPAP

TIASQPLSLRPEACRPAAGGAVHTRGLDFACDIYIWAPLAGTCGVLLLSL

VITLYCNHRNRRRVCKCPNSRLGNGVLYASVNPEYFSAADVYVPDEWEVA

REKITMSRELGQGSFGMVYEGVAKGVVKDEPETRVAIKTVNEAASMRERI

EFLNEASVMKEFNCHHVVRLLGVVSQGQPTLVIMELMTRGDLKSYLRSLR

PEMENNPVLAPPSLSKMIQMAGEIADGMAYLNANKFVHRDLAARNCMVAE

DFTVKIGDFGMTRDIYETDYYRKGGKGLLPVRWMSPESLKDGVFTTYSDV

WSFGVVLWEIATLAEQPYQGLSNEQVLRFVMEGGLLDKPDNCPDMLFELM

RMCWQYNPKMRPSFLEIISSIKEEMEPGFREVSFYYSEENKLPEPEELDL

EPENMESVPLDPSASSSSLPLPDRHSGHKAENGPGPGVLVLRASFDERQP

YAHMNGGRKNERALPLPQSSTC cDNA encoding human CD8-IGF1R fusion protein
(CD8 part (italic), IGF1R part (underlined), Kozak sequence (bold))

SEQ ID NO: 2

GCCACCATGGCCTTACCAGTGACCGCCTTGCTCCTGCCGCTGGCCTTGCT

GCTCCACGCCGCCAGGCCGAGCCAGTTCCGGGTGTCGCCGCTGGATCGGA

```
CCTGGAACCTGGGCGAGACAGTGGAGCTGAAGTGCCAGGTGCTGCTGTCC
AACCCGACGTCGGGCTGCTCGTGGCTCTTCCAGCCGCGCGGCGCCGCCGC
CAGTCCCACCTTCCTCCTATACCTCTCCCAAAACAAGCCCAAGGCGGCCG
AGGGGCTGGACACCCAGCGGTTCTCGGGCAAGAGGTTGGGGGACACCTTC
GTCCTCACCCTGAGCGACTTCCGCCGAGAGAACGAGGGCTACTATTTCTG
CTCGGCCCTGAGCAACTCCATCATGTACTTCAGCCACTTCGTGCCGGTCT
TCCTGCCAGCGAAGCCCACCACGACGCCAGCGCCGCGACCACCAACACCG
GCGCCCACCATCGCGTCGCAGCCCCTGTCCCTGCGCCCAGAGGCGTGCCG
GCCAGCGGCGGGGGCGCAGTGCACACGAGGGGGCTGGACTTCGCCTGTG
ATATCTACATCTGGGCGCCCTTGGCCGGGACTTGTGGGGTCCTTCTCCTG
TCACTGGTTATCACCCTTTACTGCAACCACAGGAACCGAAGACGTGTTTG
CAAATGTCCCAACAGCAGGCTGGGGAATGGAGTGCTGTATGCCTCTGTGA
ACCCGGAGTACTTCAGCGCTGCTGATGTGTACGTTCCTGATGAGTGGGAG
GTGGCTCGGGAGAAGATCACCATGAGCCGGGAACTTGGGCAGGGGTCGTT
TGGGATGGTCTATGAAGGAGTTGCCAAGGGTGTGGTGAAAGATGAACCTG
AAACCAGAGTGGCCATTAAAACAGTGAACGAGGCCGCAAGCATGCGTGAG
AGGATTGAGTTTCTCAACGAAGCTTCTGTGATGAAGGAGTTCAATTGTCA
CCATGTGGTGCGATTGCTGGGTGTGGTGTCCCAAGGCCAGCCAACACTGG
TCATCATGGAACTGATGACACGGGGCGATCTCAAAAGTTATCTCCGGTCT
CTGAGGCCAGAAATGGAGAATAATCCAGTCCTAGCACCTCCAAGCCTGAG
CAAGATGATTCAGATGGCCGGAGAGATTGCAGACGGCATGGCATACCTCA
ACGCCAATAAGTTCGTCCACAGAGACCTTGCTGCCCGGAATTGCATGGTA
GCCGAAGATTTCACAGTCAAAATCGGAGATTTTGGTATGACGCGAGATAT
CTATGAGACAGACTATTACCGGAAAGGAGGGAAAGGGCTGCTGCCCGTGC
GCTGGATGTCTCCTGAGTCCCTCAAGGATGGAGTCTTCACCACTTACTCG
GACGTCTGGTCCTTCGGGGTCGTCCTCTGGGAGATCGCCACACTGGCCGA
GCAGCCCTACCAGGGCTTGTCCAACGAGCAAGTCCTTCGCTTCGTCATGG
AGGGCGGCCTTCTGGACAAGCCAGACAACTGTCCTGACATGCTGTTTGAA
CTGATGCGCATGTGCTGGCAGTATAACCCCAAGATGAGGCCTTCCTTCCT
GGAGATCATCAGCAGCATCAAAGAGGAGATGGAGCCTGGCTTCCGGGAGG
TCTCCTTCTACTACAGCGAGGAGAACAAGCTGCCCGAGCCGGAGGAGCTG
GACCTGGAGCCAGAGAACATGGAGAGCGTCCCCCTGGACCCCTCGGCCTC
CTCGTCCTCCCTGCCACTGCCCGACAGACACTCAGGACACAAGGCCGAGA
ACGGCCCCGGCCCTGGGGTGCTGGTCCTCCGCGCCAGCTTCGACGAGAGA
CAGCCTTACGCCCACATGAACGGGGCCGCAAGAACGAGCGGGCCTTGCC
GCTGCCCCAGTCTTCGACCTGCTGA
```

The invention claimed is:

1. A method for the selection of a stable producer cell line expressing one or more protein(s) of interest (POIs), comprising the steps of:
   (a) providing a cell line,
   (b) concurrently stably transfecting said cell line with
       (i) a gene encoding a constitutively active variant of a growth factor receptor, wherein the variant of a growth factor receptor is a human CD8-IGF-1R fusion protein, and
       (ii) one or more gene(s) of interest (GOIs) encoding said POIs, and
   (c) cultivating said cell line in a cell culture medium either not containing the growth factor that is recognized by said growth factor receptor or containing said growth factor at concentrations which are too low to support growth of the cells in the absence of expression of said constitutively active variant of a growth factor receptor.

2. The method of claim 1, wherein the cell line is selected from the group consisting of CHO cells, HEK293 cells, CAP cells, Per.C6 cells, BHK cells, Vero cells, MDCK cells, hybridoma cells, and fibroblasts.

3. The method of claim 1, wherein the POIs are selected from the group consisting of extracellular matrix proteins, growth factors, peptide hormones, cytokines, enzymes, antibodies, antibody fragments, blood clotting factors, protease inhibitors, and viral protein products.

4. The method of claim 1, wherein the POIs are selected from the group consisting of human recombinant alpha-1-antitrypsin (rhAAT); fibrinogen; laminins (LAM); interferons (IFN); interleukins (IL); Immunoglobulin G (IgG); Immunoglobulin M (IgM); bispecific monoclonal antibodies (BsAb); erythropoietin (EPO); Factor VII (FVII); Factor VIII (FVIII); Factor IX (FIX); von-Willebrand-Factor (vWF); C1 esterase inhibitor (C1-inhibitor; C1 Inh); gag-pol from HIV-1, HIV-2, EIAV, SIV, or other retroviridae; rep protein from Adeno-Associated Virus (REP); and cap protein from Adeno-Associated Virus (CAP).

5. The method of claim 1, wherein the gene encoding a constitutively active variant of a growth factor receptor and the one or more GOIs are present on the same vector in said cell line.

6. The method of claim 1, wherein said human CD8-IGF-1R fusion protein comprises or consists of the amino acid sequence of SEQ ID NO: 1.

7. The method of claim 1, wherein said human CD8-IGF-1R fusion protein is encoded by a nucleic acid comprising or consisting of the nucleotide of SEQ ID NO: 2.

8. The method of claim 1, wherein step (c) is performed for a duration that allows selection to occur.

9. A method for the expression of one or more protein(s) of interest (POIs) in a stable producer cell line, comprising the steps of:
   (a) performing the method according to claim 1,
   (b) expressing said POIs in said stable producer cell line, and
   (c) recovering said POIs from the cells or the cell culture medium.

10. A cell comprising a polynucleotide expression construct which encodes a constitutively active variant of a growth factor receptor as a selection marker that is expressed in the cell, wherein the variant of a growth factor receptor is a human CD8-IGF-1R fusion protein, and
    wherein the polynucleotide expression construct further comprises a gene of interest that is expressed in the cell.

11. The cell of claim 10, wherein the cell is selected from the group consisting of CHO cells, HEK293 cells, CAP cells, Per.C6 cells, BHK cells, Vero cells, MDCK cells, hybridoma cells, and fibroblasts.

* * * * *

SEQUENCE LISTING

<160> NUMBER OF SEQ ID NOS: 2

<210> SEQ ID NO 1
<211> LENGTH: 622
<212> TYPE: PRT
<213> ORGANISM: Artificial sequence
<220> FEATURE:
<223> OTHER INFORMATION: human CD8-IGF1R fusion protein

<400> SEQUENCE: 1

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

-continued

```
Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Ser Leu Val Ile Thr Leu Tyr Cys Asn His
        195                 200                 205

Arg Asn Arg Arg Arg Val Cys Lys Cys Pro Asn Ser Arg Leu Gly Asn
    210                 215                 220

Gly Val Leu Tyr Ala Ser Val Asn Pro Glu Tyr Phe Ser Ala Ala Asp
225                 230                 235                 240

Val Tyr Val Pro Asp Glu Trp Glu Val Ala Arg Glu Lys Ile Thr Met
                245                 250                 255

Ser Arg Glu Leu Gly Gln Gly Ser Phe Gly Met Val Tyr Glu Gly Val
                260                 265                 270

Ala Lys Gly Val Val Lys Asp Glu Pro Glu Thr Arg Val Ala Ile Lys
            275                 280                 285

Thr Val Asn Glu Ala Ala Ser Met Arg Glu Arg Ile Glu Phe Leu Asn
290                 295                 300

Glu Ala Ser Val Met Lys Glu Phe Asn Cys His His Val Val Arg Leu
305                 310                 315                 320

Leu Gly Val Val Ser Gln Gly Gln Pro Thr Leu Val Ile Met Glu Leu
                325                 330                 335

Met Thr Arg Gly Asp Leu Lys Ser Tyr Leu Arg Ser Leu Arg Pro Glu
            340                 345                 350

Met Glu Asn Asn Pro Val Leu Ala Pro Pro Ser Leu Ser Lys Met Ile
            355                 360                 365

Gln Met Ala Gly Glu Ile Ala Asp Gly Met Ala Tyr Leu Asn Ala Asn
        370                 375                 380

Lys Phe Val His Arg Asp Leu Ala Ala Arg Asn Cys Met Val Ala Glu
385                 390                 395                 400

Asp Phe Thr Val Lys Ile Gly Asp Phe Gly Met Thr Arg Asp Ile Tyr
                405                 410                 415

Glu Thr Asp Tyr Tyr Arg Lys Gly Gly Lys Gly Leu Leu Pro Val Arg
            420                 425                 430

Trp Met Ser Pro Glu Ser Leu Lys Asp Gly Val Phe Thr Thr Tyr Ser
        435                 440                 445

Asp Val Trp Ser Phe Gly Val Val Leu Trp Glu Ile Ala Thr Leu Ala
    450                 455                 460

Glu Gln Pro Tyr Gln Gly Leu Ser Asn Glu Gln Val Leu Arg Phe Val
465                 470                 475                 480

Met Glu Gly Gly Leu Leu Asp Lys Pro Asp Asn Cys Pro Asp Met Leu
                485                 490                 495

Phe Glu Leu Met Arg Met Cys Trp Gln Tyr Asn Pro Lys Met Arg Pro
            500                 505                 510

Ser Phe Leu Glu Ile Ile Ser Ser Ile Lys Glu Glu Met Glu Pro Gly
        515                 520                 525

Phe Arg Glu Val Ser Phe Tyr Tyr Ser Glu Glu Asn Lys Leu Pro Glu
    530                 535                 540

Pro Glu Glu Leu Asp Leu Glu Pro Glu Asn Met Glu Ser Val Pro Leu
545                 550                 555                 560

Asp Pro Ser Ala Ser Ser Ser Ser Leu Pro Leu Pro Asp Arg His Ser
```

565                 570                 575
Gly His Lys Ala Glu Asn Gly Pro Gly Pro Gly Val Leu Val Leu Arg
            580                 585                 590

Ala Ser Phe Asp Glu Arg Gln Pro Tyr Ala His Met Asn Gly Gly Arg
            595                 600                 605

Lys Asn Glu Arg Ala Leu Pro Leu Pro Gln Ser Ser Thr Cys
            610                 615                 620

<210> SEQ ID NO 2
<211> LENGTH: 1875
<212> TYPE: DNA
<213> ORGANISM: Artificial sequence
<220> FEATURE:
<223> OTHER INFORMATION: cDNA encoding human CD8-IGF1R fusion protein

<400> SEQUENCE: 2

```
gccaccatgg ccttaccagt gaccgccttg ctcctgccgc tggccttgct gctccacgcc      60
gccaggccga ccagttccg ggtgtcgccg ctggatcgga cctggaacct gggcgagaca     120
gtggagctga agtgccaggt gctgctgtcc aacccgacgt cgggctgctc gtggctcttc    180
cagccgcgcg gcgccgccgc cagtcccacc ttcctcctat acctctccca aaacaagccc    240
aaggcggccg aggggctgga cacccagcgg ttctcgggca agaggttggg ggacaccttc    300
gtcctcaccc tgagcgactt ccgccgagag aacgagggct actatttctg ctcggccctg    360
agcaactcca tcatgtactt cagccacttc gtgccggtct tcctgccagc gaagcccacc    420
acgacgccag cgccgcgacc accaacaccg gcgcccacca tcgcgtcgca gcccctgtcc    480
ctgcgcccag aggcgtgccg gccagcggcg gggggcgcag tgcacacgag ggggctggac    540
ttcgcctgtg atatctacat ctgggcgccc ttggccggga cttgtggggt ccttctcctg    600
tcactggtta tcacccttta ctgcaaccac aggaaccgaa gacgtgtttg caaatgtccc    660
aacagcaggc tggggaatgg agtgctgtat gcctctgtga cccggagtga cttcagcgct    720
gctgatgtgt acgttcctga tgagtgggag gtggctcgga gaagatcac catgagccgg    780
gaacttgggc aggggtcgtt tgggatggtc tatgaaggag ttgccaaggg tgtggtgaaa    840
gatgaacctg aaaccagagt ggccattaaa acagtgaacg aggccgcaag catgcgtgag    900
aggattgagt ttctcaacga agcttctgtg atgaaggagt tcaattgtca ccatgtggtg    960
cgattgctgg gtgtggtgtc ccaaggccag ccaacactgg tcatcatgga actgatgaca   1020
cggggcgatc tcaaaagtta tctccggtct ctgaggccag aaatggagaa taatccagtc   1080
ctagcaccta caagcctgag caagatgatt cagatggccg agagattgc agacggcatg   1140
gcatacctca cgccaataa gttcgtccac agagaccttg ctgcccggaa ttgcatggta   1200
gccgaagatt tcacagtcaa aatcggagat tttggtatga cgcgagatat ctatgagaca   1260
gactattacc ggaaaggagg gaaagggctg ctgcccgtgc gctggatgtc tcctgagtcc   1320
ctcaaggatg gagtcttcac cacttactcg gacgtctggt ccttcggggt cgtcctctgg   1380
gagatcgcca cactggccga gcagccctac cagggcttgt ccaacgagca gtccttcgc   1440
ttcgtcatgg agggcggcct tctggacaag ccagacaact gtcctgacat gctgtttgaa   1500
ctgatgcgca tgtgctggca gtataacccc aagatgaggc cttccttcct ggagatcatc   1560
agcagcatca agaggagat ggagcctggc ttccggagg tctccttcta ctacagcgag   1620
gagaacaagc tgcccgagcc ggaggagctg gacctggagc agagaacat ggagagcgtc   1680
ccctggacc cctcggcctc ctcgtcctcc ctgccactgc ccgacagaca ctcaggacac   1740
```

```
aaggccgaga  acggcccgg   ccctggggtg  ctggtcctcc  gcgccagctt  cgacgagaga   1800
cagccttacg  cccacatgaa  cggggccgc   aagaacgagc  gggccttgcc  gctgcccag    1860 tcttcgacct  gctga                                                        1875
```